(12) United States Patent
Ogawa et al.

(10) Patent No.: US 6,278,760 B1
(45) Date of Patent: Aug. 21, 2001

(54) RADIATION IMAGE FORMING METHOD AND APPARATUS

(75) Inventors: Eiji Ogawa; Satoshi Arakawa, both of Kaisei-machi (JP)

(73) Assignee: Fuji Photo Film Co., Ltd., Kanagawa-Ken (JP)

( * ) Notice: Subject to any disclaimer, the term of this patent is extended or adjusted under 35 U.S.C. 154(b) by 0 days.

(21) Appl. No.: 09/434,128

(22) Filed: Nov. 5, 1999

(30) Foreign Application Priority Data

Nov. 13, 1998 (JP) .................................................. 10-323048

(51) Int. Cl.[7] ...................................................... A61B 6/03
(52) U.S. Cl. ............................... 378/5; 378/16; 378/98.11
(58) Field of Search ................................. 378/5, 16, 98.11

(56) References Cited

U.S. PATENT DOCUMENTS

| | | | |
|---|---|---|---|
| 4,709,382 | * 11/1987 | Sones | 378/62 |
| 4,896,037 | 1/1990 | Shimura et al. | 250/583 |
| 5,485,371 | 1/1996 | Ito et al. | 378/20 |
| 5,671,265 | * 9/1997 | Andress | 378/98.11 |
| 5,848,114 | 12/1998 | Kawai et al. | 378/4 |

OTHER PUBLICATIONS

"Cone beam CT–Present Status and Future Prospects", Image Information (M), pp. 122–127, Jan. 1998.

* cited by examiner

Primary Examiner—Robert H. Kim
Assistant Examiner—Allen C. Ho
(74) Attorney, Agent, or Firm—Sughrue, Mion, Zinn, Macpeak & Seas, PLLC

(57) ABSTRACT

Cone-like radiation is irradiated from each of different directions of projection to an object, and projection image signals of different energy bands are acquired with respect to the object and each of the different directions of projection. Energy subtraction processing is performed on the projection image signals of the different energy bands, which projection image signals have been acquired with respect to the same direction of projection, and an energy subtraction-processed projection image signal is thus formed with respect to each direction of projection. A three-dimensional image or a tomographic image of the object is formed from the energy subtraction-processed projection image signals, which have been formed with respect to the different directions of projection. The object image is thus formed such that a pattern of a specific structure having low contrast, such as a diseased part in the object, can be detected easily.

4 Claims, 1 Drawing Sheet

RADIATION IMAGE FORMING METHOD AND APPARATUS

BACKGROUND OF THE INVENTION

1. Field of the Invention

This invention relates to a radiation image forming method and apparatus. This invention particularly relates to a radiation image forming method and apparatus, wherein at least either one of a three-dimensional image and a tomographic image is formed from projection images having been obtained by irradiating radiation from different directions of projection to an object.

2. Description of the Prior Art

In the fields of medical images, research has heretofore been conducted to detect three-dimensional radiation image signals. As one of techniques for detecting three-dimensional radiation image signals, for example, cone-beam computed tomography (cone-beam CT) have been proposed. (The cone-beam CT is described in, for example, "Cone Beam CT—Present Status and Future Prospects," Image Information (M), pp. 122–127, January 1988; and Japanese Unexamined Patent Publication No. 9(1997)-253079.)

With the cone-beam CT, a radiation source and a two-dimensional radiation detector are rotated around an object, cone-like radiation is irradiated from the radiation source to the object, and a three-dimensional radiation image signal (i.e., a volume signal) representing the object image is acquired from radiation image signals (specifically, projection image signals), which have been detected at respective positions of rotation by the radiation detector.

In Japanese Patent Application No. 10(1998)-238737, the applicant proposed a novel radiation image detecting apparatus, which enables a volume signal free from adverse effects of scattered radiation to be obtained. With the proposed radiation image detecting apparatus, a plurality of radiation sources, which are located on a surface, are changed over successively, and radiation image signals representing radiation images of an object are detected with a radiation detector having a detection area smaller than the area of the surface, on which the radiation sources are located. Also, two-dimensional radiation image signals at predetermined positions of rotation of the radiation sources are obtained from the output signals obtained from the radiation detector. The volume signal representing the image of the object is then obtained from the two-dimensional radiation image signals.

The apparatuses for acquiring the three-dimensional radiation image signals, such as the cone-beam CT scanners and the radiation image detecting apparatus proposed in Japanese Patent Application No. 10(1998)-238737, will hereinbelow be referred to as the radiation image forming apparatuses. In the radiation image forming apparatuses, a three-dimensional image (a 3D image) of the object is formed from the acquired volume signal and displayed on an image display device, such as a cathode ray tube (CRT) display device. Also, a tomographic image is formed from the volume signal and displayed on the image display device.

However, with the radiation image forming apparatuses described above, problems are encountered in that a specific structure pattern having high contrast, such as a bone pattern, becomes perceptible, and a pattern of a diseased part of the object having low contrast cannot be detected easily.

SUMMARY OF THE INVENTION

The primary object of the present invention is to provide a radiation image forming method, wherein a radiation image of an object is formed such that a pattern of a specific structure having low contrast, such as a pattern of a diseased part in the object, may be capable of being detected easily, and the radiation image may have good image quality and can serve as an effective tool in, particularly, an efficient and accurate diagnosis of an illness.

Another object of the present invention is to provide an apparatus for carrying out the radiation image forming method.

The present invention provides a first radiation image forming method, wherein at least either one of a three-dimensional image and a tomographic image of an object is formed from projection image signals, which represent projection images of the object and which have been obtained by irradiating cone-like radiation from different directions of projection to the object, the method comprising the steps of:

i) acquiring a plurality of projection image signals of different energy bands with respect to a single object and with respect to each direction of projection, ii) performing energy subtraction processing on the plurality of the projection image signals of the different energy bands, which projection image signals have been acquired with respect to the same direction of projection, an energy subtraction-processed projection image signal being thereby formed with respect to each direction of projection, and iii) forming at least either one of the three-dimensional image and the tomographic image of the object from the energy subtraction-processed projection image signals, which have been formed with respect to the different directions of projection.

The present invention also provides a second radiation image forming method, wherein a volume signal representing an image of an object is formed from projection image signals, which represent projection images of the object and which have been obtained by irradiating cone-like radiation from different directions of projection to the object, and at least either one of a three-dimensional image and a tomographic image of the object is formed from the volume signal, the method comprising the steps of:

i) acquiring a plurality of projection image signals of different energy bands with respect to a single object and with respect to each direction of projection, ii) forming a volume signal from the projection image signals of an identical energy band having been acquired with respect to the different directions of projection, which projection image signals are among the plurality of the projection image signals of the different energy bands having been acquired with respect to the different directions of projection, a plurality of volume signals of the different energy bands being thereby formed, iii) performing energy subtraction processing on the plurality of the volume signals of the different energy bands, an energy subtraction-processed volume signal being thereby formed, and iv) forming at least either one of the three-dimensional image and the tomographic image of the object from the energy subtraction-processed volume signal.

In the first and second radiation image forming methods in accordance with the present invention, the cone-like radiation is irradiated from the different directions of projection to the object, and the projection image signals with respect to the different directions of projection are obtained. For such purposes, for example, as in the cone-beam CT, cone-like radiation may be irradiated from a radiation source and may be detected with a two-dimensional radiation detector. Alternatively, as described in Japanese Patent Application No. 10(1998)-238737, a plurality of radiation sources, which are located on a surface, may be changed over successively, and cone-like radiation as a whole may thus be irradiated to the object and may be detected with a radiation detector having a small area. (In such cases, the beam shape of the cone-like radiation is reverse to the beam shape of the cone-like radiation in the cone-beam CT). The radiation detector may be constituted of a single detection device or an array of a plurality of detection devices.

With the energy subtraction processing, a plurality of radiation images of a single object are formed with radiation having different energy levels by utilizing the characteristics such that a specific structure of the object has different levels of radiation absorptivity with respect to the radiation having different energy levels. Thereafter, a plurality of radiation image signals, which represent the radiation images of the object, are weighted, and the weighted image signals are subtracted from each other. A subtraction image signal is thus obtained, and an image, in which only the pattern of the specific structure of the object is illustrated or enhanced, is obtained from the subtraction image signal. (The energy subtraction processing is described in, for example, U.S. Pat. No. 4,896,037 and Japanese Unexamined Patent Publication No. 3(1991)-285475.)

In order for the plurality of the projection image signals of different energy bands to be acquired, one of various techniques for the energy subtraction processing may be employed. For example, a two-shot technique may be employed, wherein two exposures to radiation are performed one after the other by using radiation sources, which produce radiation of different radiation qualities, or radiation detectors, which have different radiation energy absorption characteristics. Alternatively, a one-shot technique may be employed, wherein a single, simultaneous exposure to radiation is performed by using radiation detectors, which have identical radiation energy absorption characteristics, and locating a filter, which alters the energy characteristics of the radiation, between the radiation detectors.

The present invention further provides an apparatus for carrying out the first radiation image forming method in accordance with the present invention. Specifically, the present invention further provides a first radiation image forming apparatus, wherein at least either one of a three-dimensional image and a tomographic image of an object is formed from projection image signals, which represent projection images of the object and which have been obtained by irradiating cone-like radiation from different directions of projection to the object, the apparatus comprising:

i) projection image signal acquiring means for acquiring a plurality of projection image signals of different energy bands with respect to a single object and with respect to each direction of projection, ii) energy subtraction processing means for performing energy subtraction processing on the plurality of the projection image signals of different energy bands, which projection image signals have been acquired with respect to the same direction of projection, an energy subtraction-processed projection image signal being thereby formed with respect to each direction of projection, and iii) image forming means for forming at least either one of the three-dimensional image and the tomographic image of the object from the energy subtraction-processed projection image signals, which have been formed with respect to the different directions of projection.

The present invention still further provides an apparatus for carrying out the second radiation image forming method in accordance with the present invention. Specifically, the present invention still further provides a second radiation image forming apparatus, wherein a volume signal representing an image of an object is formed from projection image signals, which represent projection images of the object and which have been obtained by irradiating cone-like radiation from different directions of projection to the object, and at least either one of a three-dimensional image and a tomographic image of the object is formed from the volume signal, the apparatus comprising:

i) projection image signal acquiring means for acquiring a plurality of projection image signals of different energy bands with respect to a single object and with respect to each direction of projection, ii) volume signal forming means for forming a volume signal from the projection image signals of an identical energy band having been acquired with respect to the different directions of projection, which projection image signals are among the plurality of the projection image signals of the different energy bands having been acquired with respect to the different directions of projection, a plurality of volume signals of the different energy bands being thereby formed, iii) energy subtraction processing means for performing energy subtraction processing on the plurality of the volume signals of the different energy bands, an energy subtraction-processed volume signal being thereby formed, and iv) image forming means for forming at least either one of the three-dimensional image and the tomographic image of the object from the energy subtraction-processed volume signal.

With the first radiation image forming method and apparatus in accordance with the present invention, the energy subtraction processing is performed on the plurality of the projection image signals of different energy bands, which projection image signals have been acquired with respect to an identical direction of projection. The energy subtraction-processed projection image signal is thus formed with respect to each of different directions of projection. Also, at least either one of the three-dimensional image and the tomographic image of the object is formed from the energy subtraction-processed projection image signals, which have been formed with respect to the different directions of projection. Therefore, an image can be obtained, in which only the pattern of a specific structure of the object is illustrated or enhanced. For example, an image signal representing an image, in which a pattern of bones has been eliminated and only a pattern of a soft tissue is illustrated, can be formed. As a result, a three-dimensional image or a tomographic image of only the soft tissue can be formed.

With the second radiation image forming method and apparatus in accordance with the present invention, the volume signal is formed from the projection image signals of an identical energy band having been acquired with respect to the different directions of projection, which projection image signals are among the plurality of the projection image signals of the different energy bands having been acquired with respect to the different directions of projection. The plurality of the volume signals of the different energy bands are thus formed. The energy subtraction processing is then performed on the plurality of the volume signals of the different energy bands, and the energy subtraction-processed volume signal is formed. Thereafter, at least either one of the three-dimensional image and the tomographic image of the object is formed from the energy subtraction-processed volume signal. Therefore, an image can be obtained, in which only the pattern of a specific structure of the object is illustrated or enhanced. For example, an image signal representing an image, in which a pattern of bones has been eliminated and only a pattern of a soft tissue is illustrated, can be formed. As a result, a three-dimensional image or a tomographic image of only the soft tissue can be formed.

As described above, with the radiation image forming methods and apparatuses in accordance with the present invention, a pattern of part of an object, which pattern is superposed upon a pattern of a specific structure having high contrast, such as a pattern of bones, and which has heretofore been hard to see, i.e. a pattern of a substance part having a different radiation absorptivity, can be separated from the pattern of the specific structure having high contrast, and an image illustrating only the separated pattern can be reproduced as a visible image. Therefore, a visible image can be obtained, which has good image quality and can serve as an effective tool in, particularly, the efficient and accurate diagnosis of an illness.

DESCRIPTION OF THE PREFERRED EMBODIMENTS

The present invention will hereinbelow be described in further detail with reference to the accompanying drawings.

Figure 1:
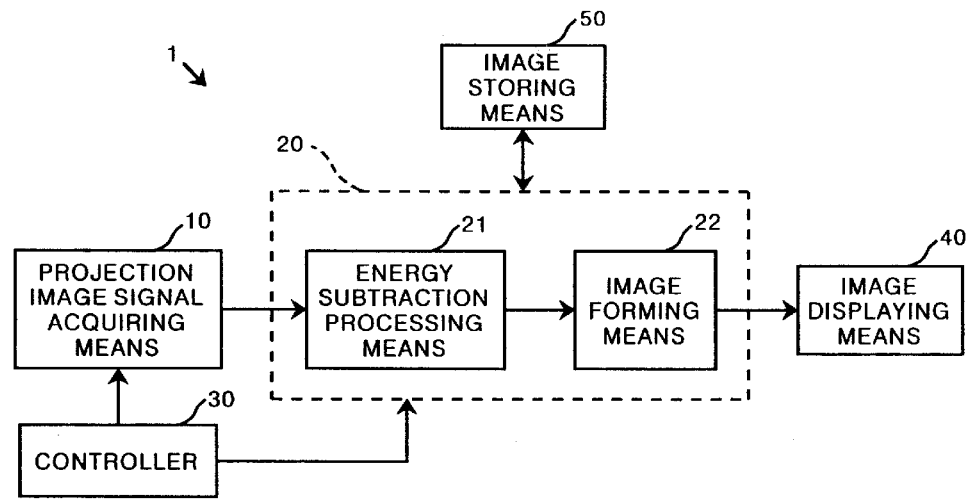
FIG. 1 is a block diagram showing an embodiment of the radiation image forming apparatus in accordance with the present invention.

FIG. 1 is a block diagram showing an embodiment of the radiation image forming apparatus in accordance with the present invention, in which energy subtraction-processed projection image signals are obtained from energy subtraction processing and a three-dimensional image or a tomographic image is formed from the energy subtraction-processed projection image signals.

With reference to FIG. 1, a radiation image forming apparatus 1 comprises projection image signal acquiring means 10 for acquiring a plurality of projection image signals of different energy bands with respect to a single object and with respect to each of different directions of projection, and an image processing section 20. The image processing section 20 comprises energy subtraction processing means 21 for performing energy subtraction processing on the plurality of the projection image signals of different energy bands, which projection image signals have been acquired with respect to an identical direction of projection. An energy subtraction-processed projection image signal is thus formed with respect to each direction of projection. The image processing section 20 also comprises image forming means 22 for forming a three-dimensional image (3D image) or a tomographic image of the object from the energy subtraction-processed projection image signals, which have been formed with respect to different directions of projection. The radiation image forming apparatus 1 is further provided with a controller 30 for controlling the projection image signal acquiring means 10, the energy subtraction processing means 21, and the like, and image displaying means 40 for reproducing and displaying the 3D image or the tomographic image as a visible image. The image processing section 20 is connected to image storing means 50 for storing various kinds of image signals.

The projection image signal acquiring means 10 is provided with radiation sources (not shown), which produce radiation having different energy characteristics. The radiation sources are changed over to one another by the controller 30. As the projection image signal acquiring means 10, the conventional cone-beam CT scanner, the apparatus described in Japanese Patent Application No. 10(1998)-238737, or the like, may be employed.

The energy subtraction processing means 21 performs the energy subtraction processing on the plurality of the projection image signals of different energy bands, which projection image signals have been acquired with respect to each direction of projection and have been read from the image storing means 50.

How the radiation image forming apparatus 1 operates will be described hereinbelow.

Firstly, the projection image signal acquiring means 10 acquires the plurality of the projection image signals of different energy bands with respect to a single object and with respect to each of different directions of projection. In order for the projection image signals to be obtained, one of various techniques may be employed. For example, with respect to a certain direction of projection, the radiation sources may be changed over to one another, and the plurality of the projection image signals of different energy bands may thus be acquired with respect to the object. Thereafter, the direction of projection may be altered, and the operation described above may be performed. In this manner, the plurality of the projection image signals of different energy bands with respect to the object may be acquired for all of the different directions of projection. Alternatively, a radiation source, which produces radiation having a certain energy level, may be utilized, and the projection image signals of the certain energy band may be acquired with respect to all of the different directions of projection. Thereafter, the radiation source may be changed over to a radiation source, which produces radiation having a different energy level, or the tube voltage of the radiation source may be changed over so as to produce radiation having the different energy level. The projection image signals of the different energy band may thus be acquired with respect to all of the different directions of projection. In this manner, the projection image signals of the different energy bands may be acquired with respect to all of the different directions of projection. As another alternative, instead of the radiation sources being changed over to one another, radiation detectors having different radiation energy absorption characteristics may be changed over to one another in order to detect the radiation carrying image information of the object. The techniques described above are the two-shot techniques. It is also possible to employ the one-shot techniques. For example, two solid-state radiation detectors having different radiation energy absorption characteristics may be superposed one upon the other and utilized to detect the radiation carrying image information of the object. Alternatively, two solid-state radiation detectors having identical radiation energy absorption characteristics may be superposed one upon the other, and a filter for altering the energy characteristics of the radiation may be located between the two solid-state radiation detectors. In this manner, the radiation before passing through the filter and the radiation after passing through the filter may be detected respectively by the two solid-state radiation detectors.

The plurality of the projection image signals of different energy bands, which have been acquired in the manner described above with respect to the single object and with respect to each of the different directions of projection, are stored in the image storing means 50.

Thereafter, the energy subtraction processing means 21 performs the energy subtraction processing on the plurality of the projection image signals of the different energy bands, which projection image signals have been acquired with respect to each direction of projection and have been read from the image storing means 50. The energy subtraction-processed projection image signal is thus formed with respect to each direction of projection. The energy subtraction processing is iterated for the projection image signals of the different energy bands, which projection image signals have been acquired with respect to all of the different directions of projection. In this manner, the energy subtraction-processed projection image signals with respect to all of the different directions of projection are acquired. The energy subtraction processing may be performed with one of various known techniques. For example, though not described in detail in this specification, the technique for the energy subtraction processing described in U.S. Pat. No. 4,896,037 or Japanese Unexamined Patent Publication No. 3(1991)-285475 may be employed.

Thereafter, the image forming means 22 forms a volume signal from the thus obtained energy subtraction processed projection image signals. The image forming means 22 then forms the 3D image or the tomographic image of the object from the volume signal. The 3D image or the tomographic image of the object is displayed on the image displaying means 40.

As described above, the volume signal is formed from the energy subtraction-processed projection image signals. Therefore, the volume signal is obtained as an energy subtraction-processed volume signal, which has been obtained from the energy subtraction processing. Accordingly, the 3D image or the tomographic image is formed as an image having been obtained from the energy subtraction processing. For example, an image, in which a pattern of bones have been eliminated and only the pattern of the soft tissue is illustrated, is obtained. Such an image is displayed as a visible image on the image displaying means 40.

In the manner described above, with the radiation image forming apparatus 1, the energy subtraction-processed projection image signals are obtained by performing the energy subtraction processing, and the 3D image or the tomographic image is formed from the energy subtraction-processed projection image signals. Therefore, a pattern of a diseased part, which is hidden behind a pattern of a specific structure, can be detected appropriately. As a result, diagnosis of an illness can be made efficiently and accurately.

Figure 2:
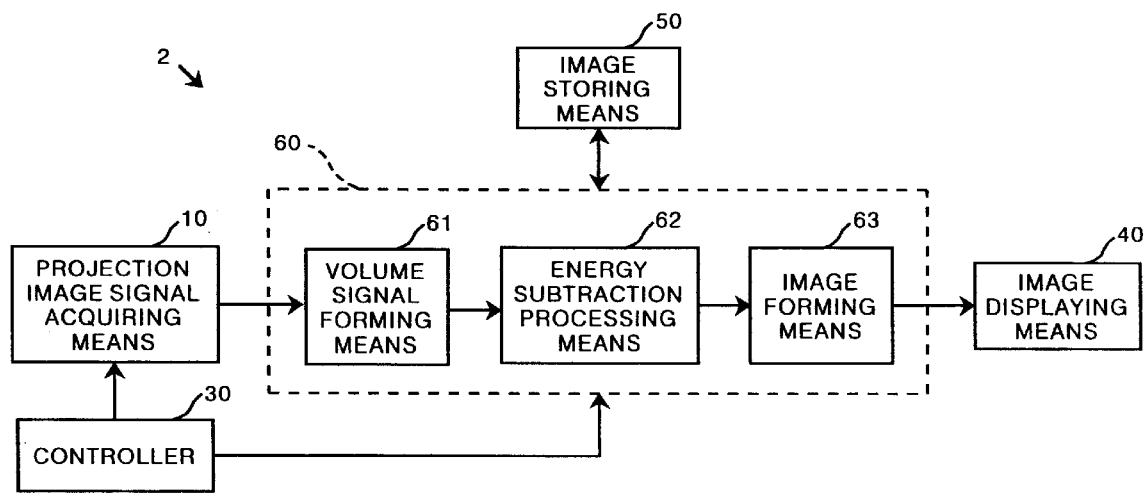
FIG. 2 is a block diagram showing a different embodiment of the radiation image forming apparatus in accordance with the present invention.

A different embodiment of the radiation image forming apparatus in accordance with the present invention will be described hereinbelow with reference to FIG. 2. In FIG. 2, similar elements are numbered with the same reference numerals with respect to FIG. 1. In the embodiment of FIG. 2, a volume signal is formed from the projection image signals of each energy band having been acquired with respect to the different directions of projection. The energy subtraction processing is then performed on a plurality of the volume signals of the different energy bands, and an energy subtraction-processed volume signal is formed. Thereafter, a 3D image or a tomographic image of the object is formed from the energy subtraction-processed volume signal.

As illustrated in FIG. 2, a radiation image forming apparatus 2 is basically constituted in the same manner as that in the radiation image forming apparatus 1, except for an image processing section 60.

The image processing section 60 comprises volume signal forming means 61, energy subtraction processing means 62, and image forming means 63. The volume signal forming means 61 forms the volume signal from the projection image signals of an identical energy band having been acquired with respect to the different directions of projection. A plurality of volume signals of the different energy bands are obtained from the volume signal forming means 61. The energy subtraction processing means 62 performs the energy subtraction processing on the plurality of the volume signals of the different energy bands and forms the energy subtraction-processed volume signal. As described above, the energy subtraction processing may be performed with one of various known techniques. The image forming means 63 forms the 3D image or the tomographic image of the object from the energy subtraction-processed volume signal.

How the radiation image forming apparatus 2 operates will be described hereinbelow.

Firstly, as in the radiation image forming apparatus 1 described above, the projection image signal acquiring means 10 acquires the plurality of the projection image signals of different energy bands with respect to a single object and with respect to each of different directions of projection. For example, two kinds of radiation sources, which produce radiation having different radiation qualities, may be employed. One of the radiation sources may comprise a 120 kV tube, a 2.5 mm-thick aluminum plate, and a 1 mm-thick copper filter. The other radiation source may comprise a 60 kv tube and a 2.5 mm-thick aluminum plate.

The plurality of the projection image signals of different energy bands, which have been acquired in the manner described above with respect to the single object and with respect to each of the different directions of projection, are stored in the image storing means 50.

Thereafter, from the image storing means 50, the volume signal forming means 61 reads the projection image signals of an energy band having been acquired with respect to the different directions of projection, which projection image signals are among the projection image signals of the two energy bands corresponding to the two kinds of the radiation qualities described above. The volume signal forming means 61 forms the volume signal from the received projection image signals of the energy band. The operation is iterated with respect to the projection image signals of the other energy band. In this manner, volume signals of the two energy bands are obtained.

Thereafter, the energy subtraction processing means 62 performs the energy subtraction processing on the volume signals of the two energy bands. Specifically, the energy subtraction processing is performed on signal components of the volume signals, which signal components represent corresponding voxels in the images represented by the volume signals. In this manner, the energy subtraction-processed volume signal representing only a soft tissue image or a bone image is formed.

Thereafter, the image forming means 63 forms the 3D image or the tomographic image of the object from the energy subtraction-processed volume signal. The 3D image or the tomographic image of the object is displayed as a visible image on the image displaying means 40.

As described above, with the radiation image forming apparatus 2, the 3D image or the tomographic image is formed from the energy subtraction-processed volume signal, which has been obtained from the energy subtraction processing. Accordingly, the 3D image or the tomographic image is formed as an image having been obtained from the energy subtraction processing. For example, an image, in which a pattern of bones have been eliminated and only the pattern of the soft tissue is illustrated, is obtained. Such an image is displayed as a visible image on the image displaying means 40.

In the manner described above, with the radiation image forming apparatus 2, the volume signal is formed from the projection image signals of each energy band having been acquired with respect to the different directions of projection. The energy subtraction processing is then performed on the plurality of the volume signals of the different energy bands, and the energy subtraction-processed volume signal is formed. Thereafter, the 3D image or the tomographic image of the object is formed from the energy subtraction-processed volume signal. Therefore, a pattern of a diseased part, which is hidden behind a pattern of a specific structure, can be detected appropriately. As a result, diagnosis of an illness can be made efficiently and accurately.

As described above, with the embodiments of the radiation image forming apparatus in accordance with the present invention, the energy subtraction processing is performed, and thereafter the three-dimensional image or the tomographic image of the object is formed. Therefore, the pattern of part of the object, which pattern is superposed upon the pattern of the specific structure and which has heretofore been hard to see, can be separated from the pattern of the specific structure, and an image illustrating only the separated pattern can be reproduced as a visible image. Therefore, a visible image can be obtained, which has good image quality and can serve as an effective tool in, particularly, the efficient and accurate diagnosis of an illness.

What is claimed is:

1. A radiation image forming method, wherein at least either one of a three-dimensional image and a tomographic image of an object is formed from projection image signals, which represent projection images of the object and which have been obtained by irradiating cone-like radiation from different directions of projection to the object, the method comprising the steps of:

i) acquiring a plurality of projection image signals of different energy bands with respect to a single object and with respect to each direction of projection, ii) performing energy subtraction processing on the plurality of said projection image signals of the different energy bands, which projection image signals have been acquired with respect to the same direction of projection, an energy subtraction-processed projection image signal being thereby formed with respect to each direction of projection, and iii) forming at least either one of the three-dimensional image and the tomographic image of the object from the energy subtraction-processed projection image signals, which have been formed with respect to the different directions of projection.

2. A radiation image forming method, wherein a volume signal representing an image of an object is formed from projection image signals, which represent projection images of the object and which have been obtained by irradiating cone-like radiation from different directions of projection to the object, and at least either one of a three-dimensional image and a tomographic image of the object is formed from the volume signal, the method comprising the steps of:

i) acquiring a plurality of projection image signals of different energy bands with respect to a single object and with respect to each direction of projection, ii) forming a volume signal from the projection image signals of an identical energy band having been acquired with respect to the different directions of projection, which projection image signals are among the plurality of the projection image signals of the different energy bands having been acquired with respect to the different directions of projection, a plurality of volume signals of the different energy bands being thereby formed, iii) performing energy subtraction processing on the plurality of said volume signals of the different energy bands, an energy subtraction-processed volume signal being thereby formed, and iv) forming at least either one of the three-dimensional image and the tomographic image of the object from said energy subtraction-processed volume signal.

3. A radiation image forming apparatus, wherein at least either one of a three-dimensional image and a tomographic image of an object is formed from projection image signals, which represent projection images of the object and which have been obtained by irradiating cone-like radiation from different directions of projection to the object, the apparatus comprising:

i) projection image signal acquiring means for acquiring a plurality of projection image signals of different energy bands with respect to a single object and with respect to each direction of projection, ii) energy subtraction processing means for performing energy subtraction processing on the plurality of said projection image signals of the different energy bands, which projection image signals have been acquired with respect to the same direction of projection, an energy subtraction-processed projection image signal being thereby formed with respect to each direction of projection, and iii) image forming means for forming at least either one of the three-dimensional image and the tomographic image of the object from the energy subtraction-processed projection image signals, which have been formed with respect to the different directions of projection.

4. A radiation image forming apparatus, wherein a volume signal representing an image of an object is formed from projection image signals, which represent projection images of the object and which have been obtained by irradiating cone-like radiation from different directions of projection to the object, and at least either one of a three-dimensional image and a tomographic image of the object is formed from the volume signal, the apparatus comprising:

i) projection image signal acquiring means for acquiring a plurality of projection image signals of different energy bands with respect to a single object and with respect to each direction of projection, ii) volume signal forming means for forming a volume signal from the projection image signals of an identical energy band having been acquired with respect to the different directions of projection, which projection image signals are among the plurality of the projection image signals of the different energy bands having been acquired with respect to the different directions of projection, a plurality of volume signals of the different energy bands being thereby formed, iii) energy subtraction processing means for performing energy subtraction processing on the plurality of said volume signals of the different energy bands, an energy subtraction-processed volume signal being thereby formed, and iv) image forming means for forming at least either one of the three-dimensional image and the tomographic image of the object from said energy subtraction-processed volume signal.

* * * * *